United States Patent
Bates et al.

(10) Patent No.: US 11,491,087 B2
(45) Date of Patent: *Nov. 8, 2022

(54) METHOD OF CAPTURING AND STABILISING THIOLS

(71) Applicant: Conopco, Inc., Trumbull, CT (US)

(72) Inventors: Susan Bates, Wirral (GB); David Mark Haddleton, Kenilworth (GB); Rachel Alice Hand, Coventry (GB); Gavin William Kirby, St Neots (GB); Ezat Khoshdel, Neston (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 43 days.

This patent is subject to a terminal disclaimer.

(21) Appl. No.: 17/045,577

(22) PCT Filed: Apr. 12, 2019

(86) PCT No.: PCT/EP2019/059468
§ 371 (c)(1),
(2) Date: Oct. 6, 2020

(87) PCT Pub. No.: WO2019/201787
PCT Pub. Date: Oct. 24, 2019

(65) Prior Publication Data
US 2021/0052471 A1    Feb. 25, 2021

(30) Foreign Application Priority Data
Apr. 18, 2018  (EP) .................... 18168038

(51) Int. Cl.
| *A61K 8/04* | (2006.01) |
| *A61Q 15/00* | (2006.01) |
| *A61K 8/49* | (2006.01) |
| *G01N 33/52* | (2006.01) |
| *G01N 21/64* | (2006.01) |

(52) U.S. Cl.
CPC .......... *A61K 8/042* (2013.01); *A61K 8/4913* (2013.01); *A61Q 15/00* (2013.01); *G01N 21/6428* (2013.01); *G01N 33/521* (2013.01); *G01N 2021/6432* (2013.01)

(58) Field of Classification Search
None
See application file for complete search history.

(56) References Cited

U.S. PATENT DOCUMENTS

| 3,843,781 A * | 10/1974 | Masuda .................... A61L 9/01 424/76.2 |
| 4,680,272 A | 7/1987 | Smith |
| 5,874,067 A | 2/1999 | Lucas et al. |
| 2018/0333515 A1* | 11/2018 | Rezai ...................... A61L 15/46 |

FOREIGN PATENT DOCUMENTS

| WO | WO03088931 | 10/2003 |
| WO | WO2009063016 | 5/2009 |
| WO | WO2015082380 | 6/2015 |
| WO | WO2018037209 | 3/2018 |

OTHER PUBLICATIONS

Search Report and Written Opinion in EP18168038; dated Jul. 30, 2018; European Patent Office (EPO).
Search Report and Written Opinion for PCTEP2019059468; Aug. 5, 2019; World Intellectual Property Org. (WIPO).
T.O. Sippel; The histochemistry of thiols and disulphides. I. The use of N-(4-aminophenyl)maleimide for demonstrating thiol groups; Histochemical Journal; Apr. 6, 1973; pp. 413-423; vol. 5; Chapman and Hall Ltd.
Mark E. B. Smith et al.; Protein Modification, Bioconjugation, and Disulfide Bridging Using Bromomaleimides; J. Am. Chem. Soc.; 2010; pp. 1960-1965; vol. 132; American Chemical Society.
Natsch et al.; Identification of Odoriferous Sulfanylalkanols in Human Axilla Secretions and Their Formation through Cleavage of Cysteine Precursors by a C—S Lyase Isolated from Axilla bacteria; Chemistry and Biodiversity; 2004; pp. 1058-1072; vol. 1.

* cited by examiner

*Primary Examiner* — Danah Al-Awadi
(74) *Attorney, Agent, or Firm* — Stephanie Huang

(57) ABSTRACT

The present invention relates to a method of capturing and stabilising volatile thiol malodour generated on the human skin, comprising steps of: i) contacting the human skin with a substrate, ii) absorbing said thiol into the substrate, and iii) reacting said thiol with a thiol-capture agent. The invention also relates to a method of quantifying said thiol, a method of assessing the deodorizing performance of a cosmetic composition on the human skin.

11 Claims, No Drawings

METHOD OF CAPTURING AND STABILISING THIOLS

CROSS REFERENCE TO RELATED APPLICATIONS

The present application is a U.S. National Phase Application under 35 U.S.C. § 371 of International Application No. PCT/EP2019/059468, filed on Apr. 12, 2019, which claims priority to European Patent Application No. 18168038.0, filed on Apr. 18, 2018, the contents of which are incorporated herein in their entireties.

FIELD OF THE INVENTION

The present invention relates to a method of capturing and stabilising volatile thiol malodour generated on human skin, a method of quantifying said thiols, a method of assessing the deodorizing performance of a cosmetic composition.

BACKGROUND OF THE INVENTION

Malodour generated on human skin, especially in the underarm area, is a well-known problem. Such malodour arises from a combination of thiols, volatile fatty acids and steroids. Thiols are particularly smelly. They are perceptible by the human nose at concentrations as low as 1-3 pg $L^{-1}$ (Natsch et al, Chem Biodivers 2004; 1, 1058-72). Current techniques employed to determine and analyze the malodour are inconvenient and problematic. The main technique is based around a group of trained 'sniffers' who smell people's underarms to determine how foul the odour is. This is only a snapshot of odour development during the day and this method is a type of non-contact sampling. The aforementioned thiols are highly volatile and with the non-contact sampling method, their true amounts and types within perspiration are not fully known. The technique is apparent not a good basis for evaluating the performance of a deodorant product. It is also difficult to map the scent profile for individuals despite suspicion that quantities and types of these volatile thiols might be different between different groups, e.g. 20-24 year males vs. 50-54 year females. In addition, 'sniffing underarm' is inconvenient and uncomfortable for both the panellists and 'sniffers'.

U.S. Pat. No. 3,843,781 describes a method for deodorizing and sweetening the smell of odoriferous materials and objects having mercaptans and hydrogen sulfide as a bad-smelling component. The method comprises applying to said material or object a series of maleimide derivatives. The maleimides are applied in an amount sufficient to substantially reduce the mercaptan and hydrogen sulfide content of the odoriferous material or object.

U.S. Pat. No. 4,680,272 describes a staining method for detecting protein molecules having amine or thiol groups, comprising halogenated maleimides and derivatives thereof. By applying the stain to a substrate suspected of containing amine or thiol groups, and applying an ultraviolet light source thereto, any fluorescence, indicative of the presence of amines or thiols, can be detected.

J. AM. CHEM. SOC. 2010, 132, 1960-65 highlights the potential for a new class of maleimide in protein modification. The report focuses on the use of mono- and dibromo-maleimides for reversible cysteine modification and illustrate this on the $SH_2$ domain of the Grb2 adaptor protein (L111C). The resultant protein-maleimide products can be cleaved to regenerate the unmodified protein by addition of a phosphine or a large excess of a thiol.

Despite all the prior art, there is no technique or method that allows the capture, stabilization and precise quantification of the volatile thiols generated on human skin. There also remains a need to assess the performance of deodorant products by evaluating how thiols are affected after the application of said products.

The present invention addresses those problems.

SUMMARY OF THE INVENTION

In a first aspect of the present invention, there is provided a method of capturing and stabilising volatile thiol malodour generated on human skin, the said method comprising steps of: i) contacting the human skin with a substrate, ii) absorbing said thiol into the substrate, and iii) reacting said thiol with a thiol-capture agent.

In a second aspect of the present invention, there is provided a method of quantifying volatile thiol malodour generated on the human skin, said method comprising the use of a method according to the first aspect of the present invention, followed by quantitative analysis of the reaction product of said thiol and said thiol-capture agent.

In a third aspect of the present invention, there is provided a method of assessing the deodorizing performance of a cosmetic composition on the human skin, said method comprising the application of said cosmetic composition to the human skin, allowing the composition to stay in contact with the skin for a given period of the time and the subsequent use of the method according to the first and second aspects of the present invention.

Herein, 'method' preferably refers to analytical and/or cosmetic method. 'Cosmetic' should be understood to mean non-therapeutic and 'cosmetic method' to mean non-therapeutic method.

Herein, 'deodorising' means controlling, suppressing, reducing, or preventing the generation of volatile thiol malodour materials on the surface of the human body.

Herein, 'volatile' means having a measurable vapor pressure at 25° C. Typically, the vapor pressure is greater than 1 or 5 Pa at 25° C.

Herein, 'thiol-capture' agent should be understood to mean an agent capable of seizing volatile thiol malodour molecules generated on human skin by chemical reaction and resulting in a stable product at ambient condition (25° C., 1 atmosphere pressure) without time constraint.

An objective of the present invention is to provide an improved method for capturing and stabilising the volatile thiol malodour materials generated on the human skin, particularly underarm areas thereof. The method is a type of contact sampling and can be used with ease and comfort. Furthermore, the method does not involve complex storage conditions (such as sub-zero degree) for the captured thiols and does not generate unpleasant species for the analyst. The captured thiols can be visibly detected in the presence of UV light. An associated objective is to provide an improved method that quantifies said thiols at very low level, such as in the range of microgram per millilitre.

Another objective of the present invention is to provide an improved method to assess the deodorising performance of cosmetic compositions on the human skin, especially deodorant compositions.

These and other aspects, features and advantages will become apparent to those of ordinary skill in the art from a reading of the following detailed description and the appended claims.

Surprisingly, it has been found that an agent can be used to capture and stabilise the volatile thiol malodours generated on human skin. The reaction product of the capturing agent and said thiol has additional benefit in that it changes colour (colourless to yellow) and has a bright spectrum, which can be precisely quantified, for example, by UV-Vis and fluorescence spectroscopy. The captured thiols can also be regenerated and released if required for further analysis.

DETAILED DESCRIPTION OF THE INVENTION

Any feature of a particular embodiment of the present invention may be utilized in any other embodiment of the invention. Any feature described as 'preferred' should be understood to be particularly preferred in combination with a further preferred feature or features. Any feature stated as preferred in a particular aspect of the invention should be understood to be a preferred feature in the other aspects of the invention. The word 'comprising' is intended to mean 'including' but not necessarily 'consisting of' or 'composed of'. The examples given in the description below are intended to clarify the invention but not to limit the invention. All weight percentages (wt %) are based upon the final weight of the composition unless indicated otherwise. Numerical ranges expressed in the format 'x-y' or 'between x and y' are understood to include x and y, unless specified otherwise. The numbers can be qualified by the term 'about'. It is understood that all ranges combining different endpoints are also contemplated.

The thiol malodour material is a compound that comprises at least one —SH group and gives out unpleasant smell. The compound is generated on the human skin, particularly the underarm regions thereof.

Thiol malodour materials that the present invention is particularly concerned with are selected from 2-methyl-3-mercaptobutan-1-ol, 3-mercaptohexan-1-ol, 3-mercaptopentan-1-ol, 3-methyl-3-mercaptohexan-1-ol, or mixtures thereof.

The present invention is a type of contact sampling, therefore the substrate suitable for contacting human skin is an essential feature. The ideal substrate can be a patch, which is tailored to the specific skin site to which it can be applied. For example, a patch can be worn in the underarm region by the testing panellist. In some preferred embodiments, a patch has an area of from 40 to 70 $cm^2$, especially when it is intended for a single patch to be applied to each single axilla of the panellist's underarm. In other embodiments, especially when it is intended for multiple patches to be applied to one axilla, the patches are preferably from 0.25 to 25 $cm^2$, more preferably 1 to 16 $cm^2$ and most preferably from 1 to 9 $cm^2$.

The thiol malodour materials are absorbed into the substrate, in most of the cases, as part of the perspiration. The adsorption typically occurs by wicking of the perspiration into the substrate.

The substrate preferably comprises an absorbent hydrogel, which is particularly useful in aiding the wicking process so that the volatile thiols are absorbed into the hydrogel layer. Herein, the term 'hydrogel' is not to be considered as limited to gels that contain water, but extend generally to all hydrophilic gels, including those containing organic non-polymeric components. The hydrogels are hydrophilic polymers characterised by their ability to absorb large amounts of aqueous fluid without dissolving in said fluid. The gel may be selected from non-ionic, anionic, cationic and zwitterionic natural hydrophilic biopolymers, synthetic hydrophilic polymers, hydrocolloids, gelling hydrophilic biopolymers and all combinations thereof. The hydrogel layer is a coherent, three-dimensional polymer capable of absorbing water without liquefying, i.e. it is insoluble in water. Usually, the insolubility in water is provided by crosslinking of a 'base' polymer, although certain hydrogel is by their nature 'crosslinked', for example, when the crosslinking occurs during the biosynthesis of the hydrogel. Herein, the 'base' polymer is to be considered the total polymer in the theoretical absence of any crosslinking agent. In practice, the 'base polymer' may never be formed; however, it may still be considered present in the hydrogel as the sum of the non-crosslinking monomers used in the synthesis.

The hydrogel comprises a hydrophilic polymer, in particular a hydrophilic polymer that is an addition polymer having pendant hydrophilic groups. Preferred hydrophilic polymer is crossed linked poly(2-acrylamido-2-methylpropane sulfonic acid) (pAMPS), poly (2-hydroxyethylmethacrylate) or one of their metal salts. A particularly preferred hydrophilic polymer is cross linked sodium poly(2-acrylamido-2-methylpropane sulfonic acid) (pNaAMPS). A non-neutralised base monomer and polymer poly(2-acrylamido-2-methylpropane sulfonic Acid®) are available from Lubrizol Corp. The preferred hydrogels can be synthesised from NaAMPS, poly(ethylene glycol)diacrylate (PEGDA) and 2-Hydroxy-2-methylpropiophenone (photoinitiator Irgacure 1173, BASF).

The thickness of the hydrogel layer may also be tailored to fit the underarm region, for example, from 1 μm to 1 cm, preferably from 0.5 to 6 mm and more preferably from 1 to 3 mm. The water content of the hydrogel layer (immediately following manufacture of the patch) is preferably from 0 to 95%, more preferably from 0 to 60% and more preferably from 0 to 40% by weight, relative to the total weight of the hydrogel (including any water present). The absorptive capacity of the hydrogel layer, as defined by its ability to absorb water at ambient temperature, is preferably from 100 or 200% by volume up to 400 or 500% by volume, based on the dry (i.e. zero water) volume of the hydrogel.

The hydrogel layer may have a sticky feel which can enhance the adhesion of the gel layer to the skin. However, this may also bring negative sensory to the wearer. The substrate preferably comprises a backing layer for the hydrogel, presenting on the outer surface of the gel. The backing layer helps to reduce the stickiness. It can also strengthen the associated hydrogel layer, thereby reducing damage.

It is preferred that the backing layer covers greater than 50% by area of the outer surface of the hydrogel layer. It is particularly preferred that the backing layer covers greater than 90% by area of the outer surface of the hydrogel layer.

The backing layer may comprise poly(alkoxyalkyl)acrylate (e.g. poly(2-hydroxyethyl)acrylate) or poly(alkoxyalkyl)methacrylate (e.g. poly(2-hydroxyethyl)methacrylate) or polyurethane. It is preferred that the backing material comprises a polyurethane elastomer and it is particularly preferred that this is the predominate materials in the backing layer. The polyurethane may be of an ester or ether based grade.

Hydrogels and backing layers as such are widely known and varied, and reference could be made to our own patent application PCT/EP2017/075994 and PCT/EP2017/075993, both of which disclose details of suitable and exemplary hydrogels and backing layers, and the contents of which should be viewed as incorporated herein.

A Thiol-capture agent is an essential feature of the present invention. The thiol capture agent is responsible for not only the capture of the volatile thiol, but also its stabilisation.

Preferably, the thiol capture agent rapidly captures and stabilises the thiol malodours via a chemical reaction, preferably a substitution reaction. The chemical reaction is preferably fast, the reaction in solution at ambient (i.e. 25° C.) may complete within 60 minutes, preferably within 30 minutes, more preferably within 10 minutes, even more preferably within 5 minutes.

In the preferred embodiments, the thiol-capture agent is selected from maleimide derivatives according to formula (I) or (II):

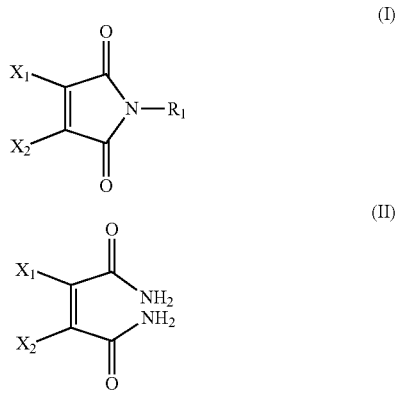

wherein $R_1$ is selected from hydrogen, C1-20 linear, branched or cyclic alkyl, alkylenyl, alkynyl or aryl residues, or hydrophilic polymers, or mixtures thereof, optionally substituted and optionally comprising one or more heteroatoms; $X_1$ is a leaving group capable of substitution by a volatile thiol malodour and $X_2$ is either a leaving group capable of substitution by a volatile thiol malodour or a hydrogen.

Herein, 'leaving group' means a molecular fragment that departs with a pair of electrons in heterolytic bond cleavage. It can be an anion or neutral molecule. In the present invention, anions are preferred.

In particularly preferred embodiments involving a thiol-capture agent according to formula (I) or (II), a substitution reaction between the volatile thiols and the thiol-capture agents happens by a nucleophilic attack on the leaving group of formula (I) and (II) by the thiols and the leaving group is subsequently eliminated. The resultant thiol-substituted product is non-volatile and is stable at ambient without time constraint. The maleimide group is known to be an effective quencher of fluorescence. However, it is found that upon thiol substitution, the quenching is eliminated and the fluorophore becomes emissive. This allows the substitution of thiols onto the thiol-capture agents to be monitored by both UV-Vis and fluorescence spectroscopy. The resultant product can also be quantified by UV-Vis or fluorescence spectroscopy, preferably fluorescence spectroscopy.

Preferably, $X_1$ is a leaving group selected from I, Br, Cl, sulphonate or substituted sulphonate and $X_2$ is also a leaving group selected from I, Br, Cl, sulphonate or substituted sulphonate or is a hydrogen. A substituted sulphonate is a salt or ester of sulphonate, for example, tosylate. More preferably, both $X_1$ and $X_2$ are leaving groups selected from I, Br, Cl, sulphonate or substituted sulphonate. Most preferably, both $X_1$ and $X_2$ are Br.

In the embodiments described in the paragraph immediately above or other preferred embodiments, the thiol-capture agent is a compound having a formula (I) and $R_1$ is H (hydrogen) or polyethylene glycol (PEG) chain. The molecular mass of PEG is typically from 0.5 to 500 KDa, preferably from 1 to 200 KDa, more preferably from 2 to 100 KDa. For example, the thiol-capture agent is a compound having a formula (I) and $R_1$ is H or PEG chain, $X_1$ is a leaving group capable of substitution by a volatile thiol malodour and $X_2$ is either a leaving group capable of substitution by a volatile thiol malodour or a hydrogen. In further preferred embodiments, the thiol-capture agent is a compound having a formula (I) and wherein $R_1$ is a hydrogen or PEG and both $X_1$ and $X_2$ are Br. In a still further preferred embodiment, the thiol-capture agent is a compound having a formula (I) and wherein $R_1$ is PEG and both $X_1$ and $X_2$ are Br. $R_1$ being PEG is particularly preferred because hydrophilic polymer such as PEG makes the thiol-capture agent readily soluble in aqueous phase (e.g. sweat) wherein the reaction may happen easily between the thiol-capture agent and thiol malodours. In this way, the need for an organic carrier can be avoided. Such carrier, for example methanol, may be unpleasant in some situations when carrying out the present invention.

The present invention preferably comprises a carrier for the thiol-capture agent. The carrier is not the aforementioned 'substrate'. The thiol-capture agent is preferably soluble in the carrier. By 'soluble' is meant a solubility of at least 0.1 g/100 mL measured at 20° C., preferably at least 1 g/100 mL, more preferably at least 10 g/100 mL. The carrier is typically a fluid, in particular a liquid at 20° C. at atmospheric pressure. A carrier can be selected from water, or an organic carrier, or mixtures thereof. A preferred organic carrier is methanol. A preferred inorganic carrier is water.

When the thiol-capture agent is used in solution, it is preferably used at a concentration from 0.01 to 100 mg/mL, more preferably from 0.1 to 10 mg/mL, still more preferably from 0.5 to 5 mg/mL.

In the most preferred embodiments, the thiol-capture agent has the formula (I), wherein both $X_1$ and $X_2$ are Br and $R_1$ is either a hydrogen or PEG. Also the concentration of such agent is subject to the preferences expressed in the paragraph immediately above.

In one way of carrying out the present invention, the thiol-capture agent is comprised in the substrate when it contacts the human skin, such as the underarm region where perspiration happens. The thiol malodour materials are absorbed into the substrate as part of the perspiration. Hence the sweat itself can act as a carrier for the thiol-capture agent. The reaction of said thiols and the thiol-capture agent happens on the substrate in such embodiments.

In another way of carrying out the present invention, the thiol-capture agent is added to the substrate after it has absorbed the thiol malodour materials from the human skin.

In yet another way of carrying out the present invention, the thiol malodour materials are absorbed into the substrate and a solvent is then used to extract said thiols from the substrate. The thiol-capture agent is added to the solvent extraction. The reaction of said thiols and thiol-capture agent may happen in the extraction. In such embodiments, the thiols and thiol-capture agent are both soluble in the solvent used for the extraction. The solvent can be inorganic and/or organic liquid, for example, water, methanol or a mixture of water and methanol.

In the method described in the paragraph immediately above, the lower limit for capturing, stabilising and/or quantifying thiol malodour is in the range of microgram per millilitre. Thus, the concentration of the thiols extracted from the human skin typically should be at least 0.05 μg/ml, preferably at least 0.5 μg/ml, more preferably at least 5

μg/ml, even more preferably at least 50 μg/ml and most preferably at least 500 μg/ml.

In each of the three ways of carrying out the present invention, the substrate may comprise an additional carrier and/or the substrate may comprise an absorbent hydrogel layer wherein additional hydrophilic liquid is provided.

The present invention also relates to a method of quantifying volatile thiol malodour generated on the human skin. Once the absorbed thiols react with the thiol-capture agent, a stable product is formed for subsequent analysis. The product changes colour (from colourless to yellow) and has a bright fluorescence spectrum, hence can be analysed by conventional techniques such as UV-Vis, fluorescence spectroscopy, preferably fluorescence spectroscopy.

It is also found that the intensity of the fluorescence is proportional to the quantity of thiol groups present, thereby permitting quantitative determination.

It is also found the captured thiol malodour materials can be released for further analysis.

This can be achieved by substitution of the captured thiol malodours with another thiol-containing material (a second thiol), typically used in large excess. Herein, 'large excess' should be understood to mean the molar concentration of the second thiol is at least 2 times to that of the already-captured thiol malodour, preferably at least 10 times, more preferably at least 20 times, most preferably at least 100 times.

In such embodiments of the present invention, the reaction product of the thiol malodour and thiol-capture agent as described in the first and second aspects of the invention, is reacting with another thiol-containing material (a second thiol).

The second thiol is added to the product of thiol malodour materials and thiol capture agent. The second thiol releases the thiol malodour by re-substitution. For example, the second thiol replaces the captured thiol on a maleimide derivative, thereby freeing the captured thiol malodours.

The release can also be monitored by techniques such as fluorescence. Because when substituted by the second thiol, the fluorescence may be deactivated due to self-quenching. The colour may change from yellow to colourless. The fluorescence spectroscopy may thus be used to monitor the progress of re-substitution as well as quantifying it.

The reaction time for full re-substitution is from 10 to 24 hours, preferably from 5 to 12 hours more preferably from 1 to 2 hours.

The released thiol malodour materials can then be characterised by other techniques if desired, for example, by GC-MS.

The second thiol can be aliphatic thiol, saturated or unsaturated cycloaliphatic thiol, or mixtures thereof. Preferably the second thiol is a phenol thiol.

The present invention also relates to a method of assessing deodorizing performance of a cosmetic composition on the human skin. The method comprises steps of application of a cosmetic composition to the human skin, allowing the composition to stay in contact with the skin for a given period of the time and the subsequent use of the method according to the first and second aspects of the present invention.

Deodorant compositions are particularly suited for assessing according to method detailed in the above paragraph. By 'deodorant composition' is meant a composition comprising a deodorant active, which may be an antimicrobial agent applied to the human skin to prevent, control, suppress, reduce malodour caused by the bacterial breakdown of perspiration, particularly in the underarm regions. Herein, deodorant active should be understood to include antiperspirant active.

Deodorant actives suitable for assessment include but are not limited to astringent active salts, including in particular aluminium, zirconium and mixed aluminium/zirconium salts, including both inorganic salts, salts with organic anions and complexes. Preferred astringent salts include aluminium, zirconium and aluminium/zirconium halides and hylohydrate salts, such as chlorohydrates. An organic antimicrobial agent may also be assessed, by which is meant an organic active that reduces microbial numbers when applied to the surface of the human body. An astringent active salt is usually present in an amount of from 0.5 to 50%, preferably from 5 to 30%, more preferably from 10 to 25% by weight of the total deodorant composition. An organic antimicrobial agent is usually present in an amount of from 0.1 to 1% by weight of the total composition.

In assessing the performance of the composition in accordance with the present invention, it is important that the cosmetic composition is left in contact with the human skin for sufficient time for it to have an effect. This is typically from 5 to 24 hours, but may be quicker in some circumstances.

The method of assessing the deodorizing performance of a cosmetic composition may further comprise a step of using the methods according to the first and second aspects of the present invention, before and after the application of a cosmetic composition to the human skin. In this way, the thiols before and after the application of the composition can both be detected, and their amounts compared. The reduction of the thiols can be used as an indication for product performance.

The method can also be applied to compare the deodorizing effect of different cosmetic compositions, simultaneously or subsequently, preferably simultaneously. For example, the performance of one deodorant composition applied to one underarm region of a panellist can be compared to the performance of another deodorant composition or a control without any deodorant actives, applied to the other underarm region of the same panellist.

The present invention may be illustrated by the following non-limiting examples.

EXAMPLES

Example 1: Synthesis of Thiol-Capture Agent

Dibromomaleimide (DBM) can be synthesized according to the method disclosed in U.S. Pat. No. 4,680,272.

N-PEG dibromomaleimide (PEG-DBM) can be synthesized according to the following method. Step 1: obtaining N-methoxycarbonyl-3,4-dibromomaleimide. To a solution of 3,4-dibromomaleimide (1.00 g, 3.9 mmol) and N-methylmorpholine (0.43 mL, 3.90 mmol) in THF (50 mL), methylchloroformate (0.30 mL, 3.90 mmol) was added and the mixture was stirred for 20 minutes at room temperature. To this mixture, dichloromethane (DCM, 40 mL) was added and the organic phase was washed with water (3×100 mL), dried with $MgSO_4$. The solvent was removed in vacuo to yield the titled product as a purple powder. $^1H$ NMR ($CDCl_3$, 300 MHz) δ (ppm): 4.01 (3H, s, $COCH_3$). $^{13}C$ NMR ($CDCl_3$, 75 MHz) δ (ppm): 131.4 (C=C), 54.8 ($COCH_3$). Step 2: N-methoxycarbonyl-3,4-dibromomaleimide (31 mg, 0.1 mmol) was dissolved in DCM (2 mL) and amino-PEG (2 kDa, 200 mg, 0.11 mmol) in DCM (2 mL) was added. The solution was stirred under nitrogen for 24 hours at ambient temperature. The resultant mixture was precipitated into cold hexane:diethyl ether (1:1) yielding PEG-dibromomaleimide as a pale off-white solid. $^1$H NMR (CDCl$_3$, 300 MHz) δ (ppm): 3.80 (2H, t, NCH$_2$CH$_2$), 3.63 (180H, s, OCH$_2$CH$_2$), 3.36 (3H, s, OCH$_3$).

Example 2: Synthesis of the Hydrogel

PolyAMPS hydrogel samples were synthesised using the following method. A batch of reaction mixture was prepared from 2-acrylamido-2-methylpropane sulfonic acid sodium salt (NaAMPS, 50% by weight in water, 46.4 g in total), poly(ethylene glycol) diacrylate (PEGDA, M$_n$~575 g mol$^{-1}$, 0.1077 g), water (30.53 g) and the photo-initiator Irgacure 1173 (2-hydroxy-2-methylpropiophenone, 0.1 ml of a 10% aqueous solution). 3 ml samples were transferred to individual moulds and then photo-cured using high intensity UV radiation from a Light Hammer® from Fusion UV Systems Corp.

Example 3: Capture and Stabilisation of Thiol Malodour, by Thiol-Capture Agent Comprised in Hydrogel The hydrogels were synthesised according to example 2. They were dehydrated for 6 hours in a 70° C. oven. Then they were rehydrated with 2 millilitre aqueous solution of DBM (0.75 mg/mL) or PEG-DBM (1.77 mg/mL).

The resultant hydrogels were left overnight, and then can be used to capture and stabilise the thiol malodours.

0.5 millilitre aqueous solution of 3-mercaptohexan-1-ol (500 µg/mL) was added to the hydrogels containing DBM or PEG-DBM. The colour change (from colourless to yellow) was viewed under a UV light.

The invention claimed is:

1. A method of quantifying volatile thiol malodour generated on the human skin, comprising the steps of:
   (i) contacting the human skin with a substrate,
   (ii) absorbing thiol malodour into the substrate,
   (iii) reacting thiol malodour with a thiol-capture agent, and
   (iv) subjecting the reaction product of said thiol and said thiol-capture agent to quantitative analysis.

2. The method according to claim 1, wherein the quantitative analysis is performed by ultraviolet light or fluorescence spectroscopy.

3. The method according to claim 2, wherein the quantitative analysis is performed by fluorescence spectroscopy.

4. The method according to claim 1, wherein the thiol malodour is a compound comprising at least one —SH group.

5. The method according to claim 1, wherein the substrate comprises an absorbent hydrogel layer comprising a hydrophilic polymer.

6. The method according to claim 1, wherein the thiol-capture agent is a compound having a formula (I) or (II):

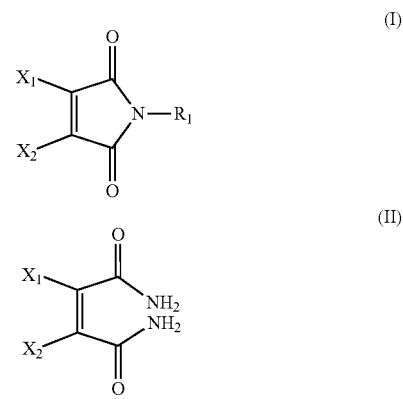

wherein R$_1$ is selected from hydrogen, C$_{1-20}$ linear, branched or cyclic alkyl, alkylenyl, alkynyl or aryl residues, or hydrophilic polymers, or mixtures thereof, optionally substituted and optionally comprising one or more heteroatoms; X$_1$ is a leaving group capable of substitution by a volatile thiol malodour and X$_2$ is either a leaving group capable of substitution by a volatile thiol malodour or a hydrogen.

7. The method according to claim 6, wherein X$_1$ is a leaving group selected from I, Br, Cl, sulphonate or substituted sulphonate and X$_2$ is also a leaving group selected from I, Br, Cl, sulphonate or substituted sulphonate or is a hydrogen.

8. The method according to claim 7, wherein both X$_1$ and X$_2$ are leaving groups selected from I, Br, Cl, sulphonate or substituted sulphonate.

9. The method according to claim 6, wherein the thiol-capture agent is a compound having a formula (I) and R$_1$ is a hydrogen or polyethylene glycol.

10. The method according to claim 9, wherein the thiol-capture agent is a compound having a formula (I) and wherein R$_1$ is a hydrogen or Polyethylene glycol and both X$_1$ and X$_2$ are Br.

11. The method according to claim 10, wherein the thiol-capture agent is a compound having a formula (I) and wherein R$_1$ is polyethylene glycol and both X$_1$ and X$_2$ are Br.

* * * * *